United States Patent
McNeill et al.

(10) Patent No.: US 11,020,264 B2
(45) Date of Patent: Jun. 1, 2021

(54) MULTI-ORIENTATION ATTACHMENT APPARATUS

(71) Applicant: Clinical Biotechnology Research Institute at RSFH, Charleston, SC (US)

(72) Inventors: Lauren McNeill, Mt. Pleasant, SC (US); Jill Nichols, North Charleston, SC (US); Andrea H. Marshall, Mt. Pleasant, SC (US)

(73) Assignee: Clinical Biotechnology Research Institute at RSFH, Charleston, SC (US)

( * ) Notice: Subject to any disclaimer, the term of this patent is extended or adjusted under 35 U.S.C. 154(b) by 0 days.

(21) Appl. No.: 16/665,927

(22) Filed: Oct. 28, 2019

(65) Prior Publication Data

US 2020/0054477 A1    Feb. 20, 2020

Related U.S. Application Data

(63) Continuation-in-part of application No. 15/898,630, filed on Feb. 18, 2018, now Pat. No. 10,456,520, which is a continuation-in-part of application No. 15/240,006, filed on Aug. 18, 2016, now Pat. No. 9,895,485.

(51) Int. Cl.
*A61F 5/44* (2006.01)
*F16B 2/08* (2006.01)
*A61F 5/451* (2006.01)

(52) U.S. Cl.
CPC ............ *A61F 5/4404* (2013.01); *A61F 5/451* (2013.01); *F16B 2/08* (2013.01)

(58) Field of Classification Search
CPC ........... A61F 5/4404; A61F 5/451; F16B 2/08
See application file for complete search history.

(56) References Cited

U.S. PATENT DOCUMENTS

| | | | | |
|---|---|---|---|---|
| 2,961,785 | A * | 11/1960 | Toepfer ................ | G09F 3/04 40/669 |
| 3,049,771 | A | 8/1962 | Litwin et al. | |
| 3,231,901 | A | 2/1966 | Kennedy | |
| 3,371,897 | A | 3/1968 | Serany, Jr. et al. | |
| 3,438,095 | A * | 4/1969 | Evans ................... | B65D 63/10 24/16 PB |
| 3,568,980 | A * | 3/1971 | Hulburt ................ | A01K 3/005 256/10 |
| 4,466,159 | A * | 8/1984 | Burrage ............... | B65D 63/10 24/16 PB |
| 4,823,444 | A | 4/1989 | Larsen | |
| 4,896,465 | A | 1/1990 | Rhodes et al. | |
| 4,979,714 | A | 12/1990 | Russell et al. | |
| 5,005,793 | A | 4/1991 | Shillington | |
| 5,135,188 | A | 8/1992 | Anderson et al. | |

(Continued)

*Primary Examiner* — Anita M King
(74) *Attorney, Agent, or Firm* — Gregory Finch; Finch Paolino, LLC

(57) ABSTRACT

A multi-orientation attachment apparatus constructed of molded silicone or another form of elastomeric substance and configured to be selectively coupled to a variety of hospital surfaces. Embodiments of the present disclosure may include two or more pairs of elongated members being configured to be selectively coupled to a circumference, for instance, a hospital bed rail or an IV pole, at a first end and selectively coupled to form a loop at a second end.

20 Claims, 19 Drawing Sheets

(56) References Cited

U.S. PATENT DOCUMENTS

| | | | |
|---|---|---|---|
| 5,344,107 A | 9/1994 | Lee | |
| 5,395,018 A * | 3/1995 | Studdiford | B62H 5/00 224/420 |
| 5,581,850 A * | 12/1996 | Acker | F16L 3/23 24/16 PB |
| 5,699,642 A * | 12/1997 | McDevitt, Jr. | E04C 5/162 24/16 PB |
| D391,636 S | 3/1998 | Zwerk | |
| 6,186,454 B1 | 2/2001 | Olsen | |
| 6,409,131 B1 | 6/2002 | Bentley et al. | |
| 7,241,071 B2 * | 7/2007 | Carraher | E04C 5/163 403/164 |
| 7,475,859 B2 | 1/2009 | Selders | |
| 7,731,138 B2 | 6/2010 | Wiesner et al. | |
| D619,887 S * | 7/2010 | Colton | B65D 63/10 D8/396 |
| 7,913,959 B2 | 3/2011 | White et al. | |
| 7,959,122 B1 | 6/2011 | Clack-Hopkins | |
| 8,245,857 B2 | 8/2012 | DiGasbarro | |
| 9,204,710 B1 * | 12/2015 | Burns | F16M 11/242 |
| 9,386,824 B1 | 7/2016 | Schultz | |
| D848,616 S * | 5/2019 | McNeill | A01K 3/005 D24/128 |
| 10,456,520 B2 * | 10/2019 | McNeill | A61G 7/05 |
| 2002/0060275 A1 * | 5/2002 | Polad | F16L 3/137 248/74.3 |
| 2002/0096608 A1 | 7/2002 | Cedarberg, III | |
| 2003/0167605 A1 | 9/2003 | Schultz | |
| 2007/0282272 A1 | 12/2007 | Bannon et al. | |
| 2008/0011907 A1 | 1/2008 | Jacobsma | |
| 2010/0243834 A1 | 9/2010 | Salser | |
| 2011/0084181 A1 | 4/2011 | Bowers et al. | |

* cited by examiner

MULTI-ORIENTATION ATTACHMENT APPARATUS

CROSS-REFERENCE TO RELATED APPLICATIONS

The present application is a continuation-in-part of U.S. patent application Ser. No. 15/898,630, filed on Feb. 18, 2018 and entitled "Stretchable Attachment Apparatus," which is a continuation-in-part of U.S. patent application Ser. No. 15/240,006, filed on Aug. 18, 2016 and entitled "Stretchable IV Pole Attachment Apparatus," now U.S. Pat. No. 9,895,485. Both of the above-cited applications are hereby incorporated in their entireties, at least by reference.

FIELD

The present disclosure relates to the field of medical devices accessories; in particular, apparatuses for selective attachment to various hospital equipment.

BACKGROUND

Infection control is an ever-increasing concern in hospital environments. Harmful infectious diseases can be spread by contact with a patient's contaminated body fluids. Healthcare providers are constantly on a quest to minimize the risk of exposure to harmful organisms. Bladder bags present a unique problem in that unlike IV bags, which hang from a hook above a patient's heart on a IV pole, bladder bags must utilize the effects of gravity and hang below the patient to function correctly. Because of this necessity, the bladder bag cannot be placed on the higher hooks of the IV pole and are generally hung over the side of the patient's bed. These bags are not sterile and function to hold the waste products from the patient. Accidental leakage from these bags can unknowingly contaminate the hospital furniture and potentially expose healthcare workers and family members to infectious diseases. Similarly, following surgeries or discharge from the ICU, patients are required to ambulate while still in the hospital. Many of these patients are encumbered with catheters, IV's, bladder bags, chest drainage boxes, or the like. These laden devices and tubing can be difficult to maneuver with, especially for those patients that are of a fragile state, both mentally and physically. A patient ambulating with a chest tube and being asked to carry a heavy chest drainage box is a potential safety hazard to both the patient, healthcare workers and visitors due to the stress on the patient to not drop or tip over the chest drainage box. Ambulating while attached to a ventilator is a potential safety hazard to the patient due to the excessive tubes that are delicately attached to the patient and the strain of their weight on the patient while standing upright. Proper handling of these tubes and devices are dependent on the due diligence of the healthcare workers to manage them on behalf of the patient to prevent the patient from tripping, a potentially devastating scenario.

A review of the prior art reveals several different types of fasteners for an IV pole. For example, U.S. Pat. No. 6,409,131 B1 issued to Bentley and Rosenau discloses a bracket that attaches to an elongated prop such as an electrical conduit, pipe, railing, IV stand, wheel chair frame, stake, hospital bed guards, or post is disclosed.

U.S. Pat. Publ. No. US20110084181 A1 discloses a Pole Universal Drainage Bag Holder. It works as a collaboration of the following parts: The Camp Front Opening, the Middle Holding Section and the Clamp Handles. The clamp front opening is used to hold a catheter or I.V. bag or a drainage bag of any general size.

U.S. Pat. Publ. No. US20100243834 A1 discloses an adjustable clamp that can attach to an IV pole.

U.S. Pat. Publ. No. US20080011907 A1 discloses an intravenous line organizer clamped to an IV pole.

U.S. Pat. No. 7,731,138 B2 discloses a mounting apparatus with a flexible shaft with a first end for releasable attachment to the support member and a second end for releasable attachment to the device. A generally C-shaped clamping member at the first end releasably attaches the apparatus to the support member.

U.S. Pat. No. 7,475,859 B2 discloses a band buckled around a pole. A hanger arm has a top end attached to the band at an attachment point, and has a bottom end with a load hook.

U.S. Pat. No. 8,245,857 B2 discloses a storage device including a locking slot formed in an upper portion adapted to receive at least a portion of the instrument to retain the instrument within the housing.

U.S. Pat. No. 4,823,444 discloses a device pertaining primarily to supplementary fastening devices in the form of a rigid or semi rigid clip having a loop shaped portion for fastening the hook of a garment hanger or other hook including device to a clothesline or other generally linear member to which the hook is hooked.

U.S. Pat. Publ. No. 20030167605 A1 discloses a fastening strap system, particularly of the hook-and-loop variety (with hooks on one side of the strap and loops on the other side), for selectively and independently binding and/or releasing a plurality of sets of essentially longitudinal objects such as wires, from one another.

U.S. Pat. No. 6,186,454 B1 discloses a sign housing mounted to a swivally-mounted base and a pair of flexible and resilient, semi-circular parts are integrally formed with the base.

U.S. Pat. No. 5,005,793 discloses a pole dip needle cap holder.

U.S. Pat. No. 7,959,122 B1 discloses a catheter drainage bag holding assembly includes a clamp with an arcuate member having a pair of free ends. The arcuate member forms at least 60% of a complete circle. A threaded rod is threadably coupled to and extends through the arcuate member. The arcuate member is positionable on a post and the rod is abuttable against the post.

U.S. Pat. No. D391636 S discloses a catheter pole attachment utilizing a nut and bolt anchoring system.

U.S. Pat. No. 7,913,959 B2 discloses a suction nozzle holster.

U.S. Pat. No. 5,135,188 A discloses a bundling strap for enclosing an article such as a wire or group of wires comprising a strap of flexible material having integrally formed along one face thereof a row of ratchet-like teeth, an enclosure formed at one end of said strap and projecting in a direction transverse thereto.

U.S. Pat. No. 3,231,901 A discloses a drain bag hanger which utilizes metal clamps and link chain.

U.S. Pat. Publ. No. US 20020096608 A1 discloses a holder with a base rotatably mounted to the IV stand. An arm is supported by the base and extends away from the base such that the arm holds the cords and the tubes extending from the medical apparatus.

U.S. Pat. No. 9,386,824 B1 discloses a strap system being constructed of a material that sticks to itself, such as VELCRO, for selectively and independently binding and/or releasing at least one set of essentially longitudinal objects, such as wires, from one another.

U.S. Pat. No. 4,896,465 A discloses a clip like device made of two layers of a foam material mounted between supports that allow a range of use cases to be secured between the foam layers. The use of an adhesive surface or elastic strap can be utilized to mount the support to a pole, wrist, surgical tray, drape, wall, or the like.

U.S. Pat. No. 4,979,714 discloses a hangerclip in the shape of a closed "S" with symmetrical tear drop loops for hanging IV bags.

U.S. Pat. No. 5,344,107 A discloses a tube strap with a first end having a hole for accommodating a tube and a second hook end. The strap can be used as a hanger with the hook engaging a support arm or tube.

U.S. Pat. No. 3,049,771 A discloses a self-locking holder, band or clamp in the form of a strap formed of flexible plastic material. The locking mechanism is by means of a buckle created by a tongue engaging with interlocking teeth.

U.S. Pat. No. 337,897 A discloses a drainage bag support comprising of a flexible strap for use in hanging the support from a bed rail or the like.

U.S. Pat. Publ. No. 2007/0282272A1 discloses a device for guiding and/or organizing medical tubing for use in a hospital, especially associated with a rail of a hospital bed, an intravenous pole, portion of a wheelchair, or a sheet material associated with the bed or patient.

The patent documents above disclose a myriad of attachment mechanisms to be used on an IV pole. However, due to the nature of these designs having multiple parts and crevices, a large surface area is created that is not easily decontaminated for infection control purposes. In addition, many of the devices are made of materials in which regular disposal would not be economically efficient.

In addition to attachment mechanisms for IV poles, medical personnel commonly attach a multitude of various objects to different surfaces in a hospital room environment. One such surface is a bed rail of a hospital bed. As with prior art solutions for attachment mechanisms to be used on an IV pole, prior art solutions for attachment mechanisms to be used on hospital bed rails encounter similar problems with respect to effective decontamination and economically efficient regular disposal.

Through applied effort, ingenuity, and innovation, Applicant has identified a number of deficiencies and problems with infection control with regards to the attachment mechanisms for patient intravenous and catheter networks in the healthcare environment. Applicant has developed a solution to address these deficiencies and problems, and is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is the continuous molded structure of the body that allows for easy decontamination of a multi-orientation strap apparatus. Another object of the present disclosure is that the elastomeric material and simple body design make disposal of the multi-orientation strap apparatus economically feasible.

Another object of the present disclosure is a multi-orientation strap apparatus being constructed of an elastomeric material that enables the multi-orientation strap apparatus to maintain a sturdy connection with the terminus to which it is selectively attached.

Another object of the present disclosure is a multi-orientation strap apparatus addressing multiple use-case scenarios with a single device to allow for greater flexibility to healthcare workers and patients.

An embodiment of the present disclosure is molded into a single continuous elastomeric body configured to enable efficient surface decontamination via a smooth, continuous construction. In addition, the elastomeric design and construction allows for economic efficiency to regularly discard and replace the apparatus.

A specific embodiment of the present disclosure includes a multi-orientation strap apparatus comprising a unitary body constructed of an elastomeric material, the unitary body comprising a first appendage portion, a second appendage portion, a third appendage portion, a fourth appendage portion, and a central portion located between the first appendage portion and the second appendage portion and between the third appendage portion and the fourth appendage portion; a plurality of protrusions disposed on the first appendage portion and the third appendage portion, the plurality of protrusions being substantially rectangular in shape; wherein the second appendage portion extends from the central portion, the second appendage portion being oppositely oriented from the first appendage portion, the second appendage comprising a first attachment portion configured to receive at least one protrusion in the plurality of protrusions; and wherein the fourth appendage portion extends from the central portion, the fourth appendage portion being oppositely oriented from the third appendage portion, the fourth appendage comprising a second attachment portion configured to receive at least one protrusion in the plurality of protrusions.

Another specific embodiment of the present disclosure includes a multi-orientation strap apparatus comprising a pair of elongated members constructed of a molded elastomeric material, wherein the first protrusion located on the first appendage portion is selectively configured to extend through the aperture of the first receiving portion located on the second appendage portion such that the first attachment area is configured to define a loop, wherein the first protrusion located on the third appendage portion is selectively configured to extend through the aperture of the first receiving portion located on the fourth appendage portion such that the second attachment area is configured to define a loop.

Further specific embodiments of the present disclosure provide for a multi-orientation strap apparatus comprising a unitary body comprising a central portion and a first appendage, a second appendage and third appendage and a fourth appendage extending outwardly from the central portion, the unitary body defining an X-shape; a plurality of protrusions being disposed on the first appendage and the second appendage; and a plurality of apertures being disposed on the third appendage and the fourth appendage, wherein each protrusion in the plurality of protrusions is configured to selectively interface with each aperture in the plurality of apertures.

Still further specific embodiments of the present disclosure provide for a multi-orientation strap apparatus comprising at least four appendages being coupled together to define a unitary body, at least a first pair of appendages in the at least four appendages being selectively coupled together to define a first loop, and at least a second pair of appendages in the at least four appendages being selectively coupled together to define a second loop, the first loop and the second loop being oppositely oriented.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
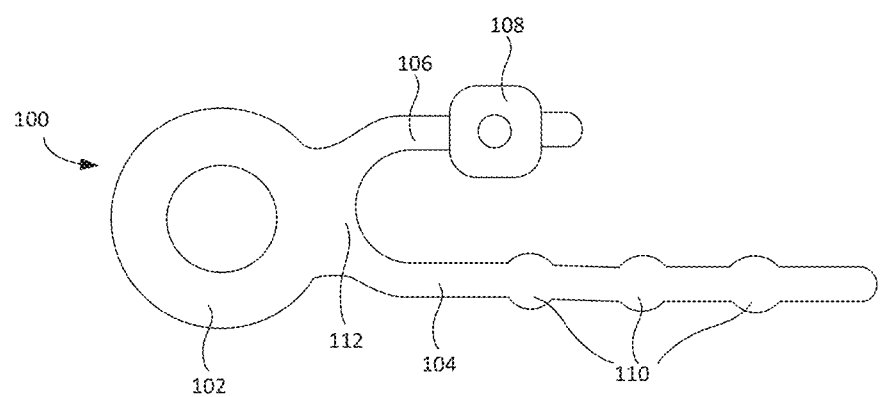
FIG. 1 is a perspective view of the IV pole attachment apparatus according to an embodiment of the present disclosure.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure provide for a disposable IV pole attachment apparatus. Embodiments of the present disclosure solve problems associated with the prior art IV pole attachment devices. Most of the designs of the prior art attachment devices are not conformed to hold patient bladder bags to IV poles. The designs that could be utilized either have large surface areas with various moving parts which make them difficult to decontaminate effectively, or the materials used to make them are not conducive to the device being manufactured as a disposable product. A disposable attachment apparatus is desirable as the contents of a bladder bag can accidentally leak onto the structure to which it is attached. Harmful bacteria and viruses can be secreted in body fluids; therefore, it is important to decontaminate any items exposed to body fluids for proper infection control. Prior art attachment devices present with various hooks and screws that increase the surface area of the device and allow for small crevices, which can be difficult to decontaminate. Without proper infection control, healthcare workers and subsequent patients and visitors are placed at risk.

Another problem with the prior art is the complex design and materials used to make the attachment devices. An IV Pole attachment with various hooks and buckles is not as easily manufactured as one molded into a single piece. In addition, attachment devices made of metal are costlier to manufacture and are generally recycled and not disposed.

Embodiments of the present disclosure seek to overcome the deficiencies of the prior art and provide a more efficient, cost effective, and safe IV pole attachment apparatus. According to various embodiments of the present disclosure, the problem of large surface areas and crevices is solved by the molded continuous body of the IV Pole attachment apparatus. The continuous body of the apparatus can be easily disinfected or wiped down, as there are no parts containing crevices that could hold contaminated fluids.

According to various embodiments of the present disclosure, the problems of a complex design is solved by a simple one-piece body of molded elastomeric material. Further, this elastomeric material is inexpensive which in turn makes it economically feasible to produce the apparatus as a disposable product. A disposable product is always the preferred method of infection control in hospital settings.

Referring now to FIG. 1, a top perspective view of an IV pole attachment apparatus 100 is shown. According to an embodiment, device 100 is generally comprised of an attachment portion 102, a first appendage 104, a second appendage 106, a receiving portion 108, protrusions 110, and an appendage connection portion 112. The IV pole attachment apparatus 100 is constructed of silicone or another form of elastomeric substance. The elastomeric substance of IV pole attachment apparatus 100 may be alternatively constructed from a flexible antimicrobial substance or combination thereof. One end of IV pole attachment apparatus 100 is the attachment portion 102. Attachment portion 102 is ring-shaped; it may be alternatively constructed in a different geometric shape, such as square, triangle, rectangle, irregular, and the like. The shape of attachment portion 102 can be any commercially viable shape capable of receiving a hook from a bladder bag. The silicone of attachment portion 102 is substantially thicker than the silicone of the appendage portions. The silicone of attachment portion 102 may be approximately 20% to 200% thicker than the silicone of the appendage portions 104 and 106. This increase in thickness allows the attachment portion 102 to support the weight of an attached bladder bag. Attachment portion 102 is seamlessly molded to the appendage connection portion 112. Appendage connection portion 112 is seamlessly connected to the first appendage 104 and the second appendage 106. The first appendage 104 contains three spaced protrusions 110 molded into the appendage in a linear consecutive arrangement. The first appendage 104 may be alternatively constructed to contain more or less protrusions, depending on the length of first appendage 104. The protrusions 110 are spherical in shape. The protrusions 110 may be alternatively constructed in various shapes, such as cylindrical, irregular, star-shaped, and the like. The first appendage 104 is pulled through the aperture of the receiving portion 108. The protrusions 110 that line the first appendage 104 are greater in diameter than the aperture of the receiving portion 108. The elastomeric material allows the protrusions 110 to be forced through the aperture of the receiving portion 108. The greater diameter of the protrusions 110 keeps them from easily passing back thorough the aperture of the receiving portion 108 and allows for a buckling action that secures the IV pole attachment apparatus 100 to an IV pole. The second appendage 106 is approximately half the length of the first appendage 104. The second appendage 106 may be alternatively constructed in a longer length. The second appendage 106 contains a receiving portion 108 seamlessly molded into the appendage. The receiving portion 108 is square. The receiving portion 108 may be alternatively constructed in another geometric shape. The receiving portion 108 is constructed to provide for an aperture capable of receiving a spherical protrusion 110 from first appendage 104. The receiving portion 108 may be alternatively constructed to provide for an aperture capable of receiving a protrusion of a different geometric shape. The diameter of the aperture within the receiving portion 108 is less than the diameter of the protrusions 110.

Figure 2:
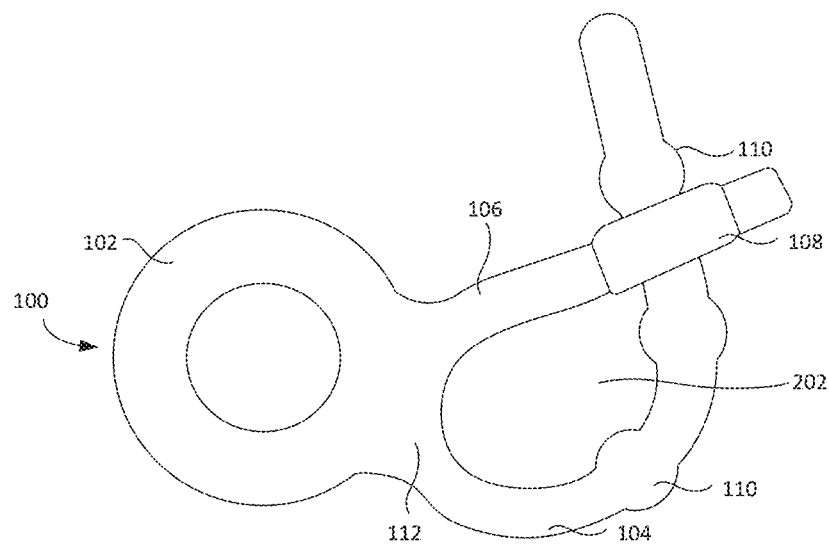
FIG. 2 is a perspective view thereof, according to an embodiment.

Referring now to FIG. 2, a top perspective view of the IV pole attachment apparatus 100 in a locking position is demonstrated. According to an embodiment of the present disclosure, protrusions 110 are molded into the first appendage 104. A protrusion 110 on the first appendage 104 is pulled through the aperture of the receiving portion 108. The greater diameter of the protrusion 110 allows the first appendage 104 and the second appendage 106 to maintain a buckled position as shown. This buckled position causes the appendage connection portion 112 to form a U-shape attachment loop 202. The attachment loop 202 fits flush against the IV pole.

Figure 3:
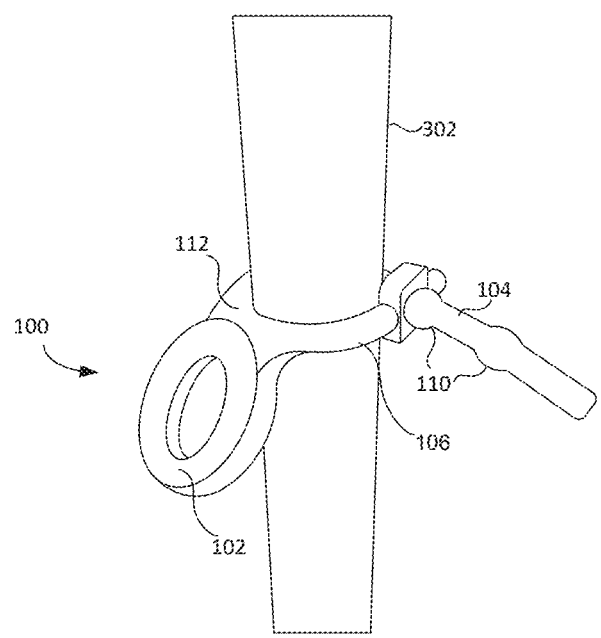
FIG. 3 is a perspective in-use view thereof, according to an embodiment.

FIG. 3 is a side perspective view of the IV pole attachment apparatus 100 attached to an IV pole 302. The IV pole attachment apparatus 100 is buckled onto the IV pole 302 by placing the appendage connection portion 112 flush against the IV pole 302 and pulling the first appendage 104 through the aperture of the receiving portion 108 of the second appendage 106. The sides of the receiving portion 108 must be pulled apart in order to increase the diameter of the aperture and allow a protrusion 110 on the first appendage 104 to pass through. Once the protrusion 110 is pulled through the aperture of the receiving portion 108, the elastomeric material reforms a smaller diameter aperture, in turn restricting the passage of the protrusion 110 back through the receiving portion. As shown, the IV pole attachment apparatus 100 is in this buckled position. The apparatus connection portion 112, the second appendage 106, and the upper portion of the first appendage 104 sit flush against the IV pole 302 when the IV pole attachment apparatus 100 is in the buckled position. As shown, attachment portion 102 is formed as a circular structure thicker in elastomeric material than the first appendage 104 and the second appendage 106. This thickness allows the attachment portion 102 to withstand the weight of a filled bladder bag. The IV pole attachment apparatus 100 is easily removed from the IV pole 302 for decontamination or disposal. To remove the IV pole attachment apparatus 100, the elastomeric material of the receiving portion 108 is pulled apart to form an aperture large enough for the first appendage 104 and the protrusion 110 to pass back through. The unbuckling releases the IV pole attachment apparatus 100 from the IV pole 302.

Figure 4:
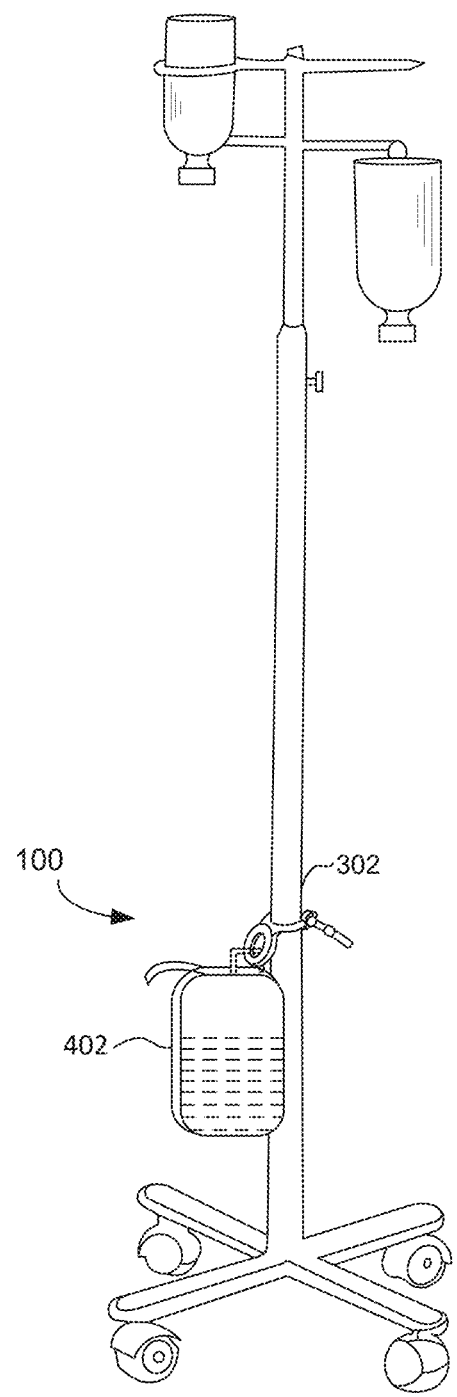
FIG. 4 is a perspective in-use view thereof, according to an embodiment.

FIG. 4 is a perspective in-use view of the IV pole attachment apparatus 100. FIG. 4 demonstrates how the bladder bag 402 hooks onto the IV pole attachment apparatus 100. This provides for a more sanitary way to maintain the bladder bag 402 while still having the bladder bag 402 positioned below the patient for proper functioning. The IV pole attachment apparatus 100 provides a place to hang the bladder bag other than on the patient or the room furniture. The use of the IV pole attachment apparatus 100 improves infection control by preventing contamination of the patient's clothing and furniture due to accidental leakage. Due to the simple continuous body of the IV pole attachment apparatus 100, it is easily disinfected or disposed of after use.

Hospital Bed Rail Attachment Apparatus

An alternative embodiment of the present disclosure provides for a disposable hospital bed rail attachment apparatus. Embodiments of the present disclosure solve problems associated with the prior art hospital bed rail attachment devices. Most of the designs of the prior art attachment devices either have large surface areas with various moving parts which make them difficult to decontaminate effectively, or the materials used for construction are not conducive to being manufactured as a disposable product. A disposable attachment apparatus is desirable as the surfaces adjacent to a hospital bed are prone to contamination. According to various embodiments of the present disclosure, the problem of multi-piece construction is solved by a one-piece body of molded elastomeric material. Elastomeric material is inexpensive which makes regular disposal and replacement of the apparatus economically feasible, as compared to prior art solutions.

Figure 5:
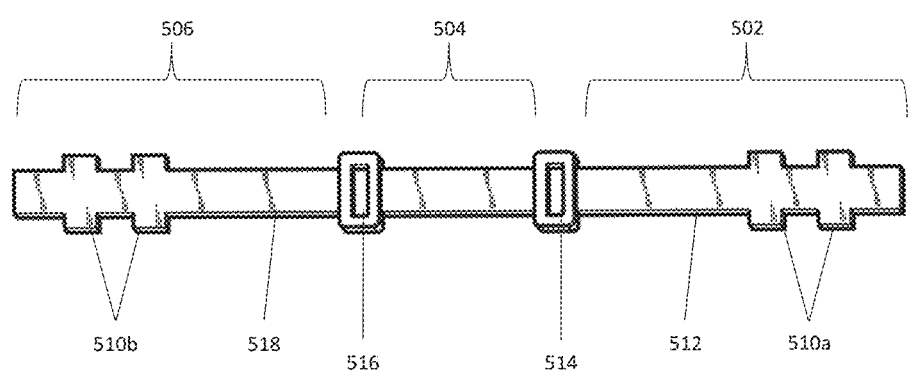
FIG. 5 is a perspective view of a hospital bed rail attachment apparatus, according to an alternative embodiment of the present disclosure.

Referring now to FIG. 5, a perspective view of a hospital bed rail attachment apparatus 500 is show. According to an embodiment, hospital bed rail attachment apparatus 500 is configured as an elongated member constructed of a molded elastomeric material. Hospital bed rail attachment apparatus 500 may be generally comprised of a first appendage portion 502, a second appendage portion 506, and a central portion 504 extending between first appendage portion 502 and second appendage portion 506. First appendage portion 502 may be configured to define at least one protrusion 510a and a first receiving portion 514. A first attachment area 512 may be defined by a length of first appendage portion 502 extending between protrusion 510a and first receiving portion 514. Second appendage portion 506 may be configured to define at least one protrusion 510b and a second receiving portion 516. A second attachment area 518 may be defined by a length of second appendage portion 506 extending between protrusion 510b and second receiving portion 516.

Protrusions 510 may be substantially rectangular in shape; however, the shape of protrusions 510 is a design choice, and may be configured as a multitude of alternative shapes. In an embodiment, hospital bed rail attachment apparatus 500 includes two protrusions 510a disposed on first appendage portion 502, and two protrusions 510b disposed on second appendage portion 506. Alternatively, there may be as few as one protrusion 510 or a plurality of protrusions 510 disposed on either of first appendage portion 502 or second appendage portion 506. Protrusions 510 should be wider in width than that of central portion 504. First receiving portion 514 and second receiving portion 516 each have an aperture configured to receive protrusions 510. The aperture of first receiving portion 514 and second receiving portion 516 may be substantially oblong in shape; however, the shape of the aperture of first receiving portion 514 and second receiving portion 516 is a design choice and may be configured as any shape suitable to receive and hold protrusions 510. Hospital bed rail attachment apparatus 500 is configured such that a user may insert the end of first appendage portion 502 into the aperture of first receiving portion 514 and pull protrusion 510 therethrough. Likewise, hospital bed rail attachment apparatus 500 is configured such that a user may insert the end of second appendage portion 506 into the aperture of second receiving portion 516 and pull protrusion 510 therethrough. The elastomeric material utilized in the construction of hospital bed rail attachment apparatus 500 should be of a hardness and elasticity such that protrusions 510 are substantially stretchable to be pulled through first receiving portion 514 or second receiving portion 516, but are substantially hard enough to maintain a connection with first receiving portion 514 or second receiving portion 516 when engaged to support a desired load capacity of an attached object.

Figure 6:
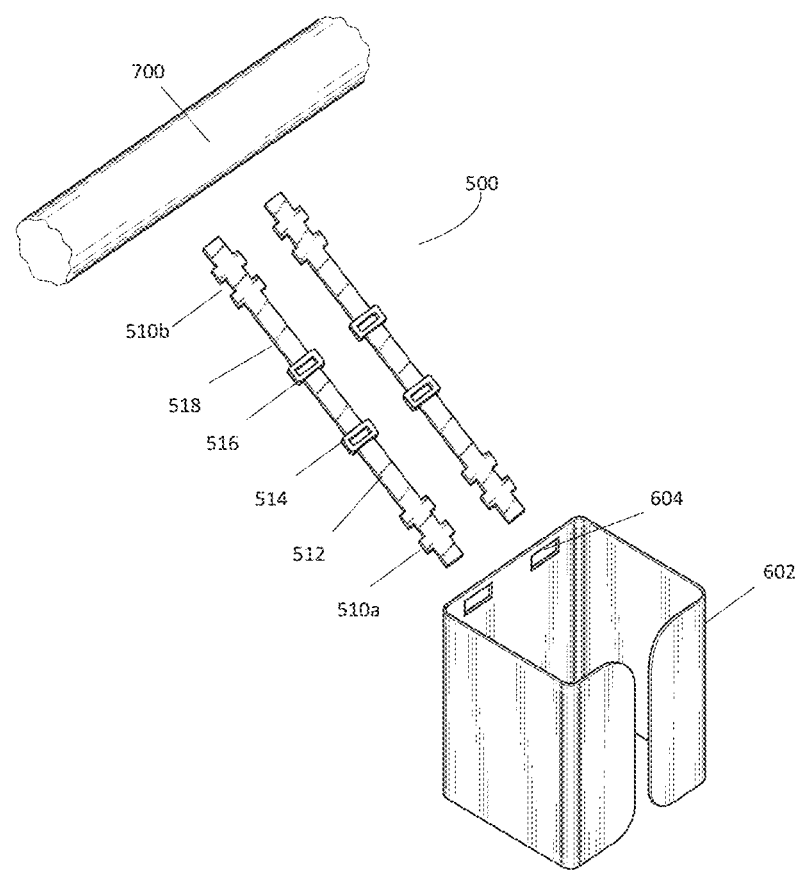
FIG. 6 is a perspective view of a hospital bed rail attachment apparatus used in combination with an attachable container.
Figure 7:
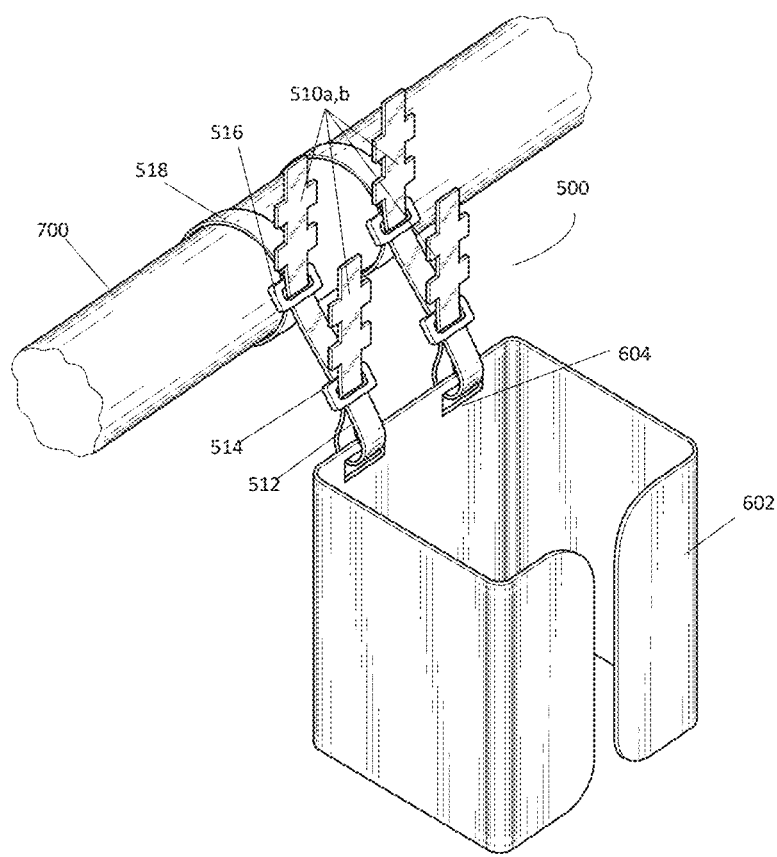
FIG. 7 is a perspective in-use view thereof, according to the embodiment of FIG. 6.

Referring now to FIGS. 6 and 7, a perspective view of hospital bed rail attachment apparatus 500 as used in combination with an attachable container 602 is shown. Referring first to FIG. 6, a pair of hospital bed rail attachment apparatuses 500a and 500b are utilized to attach a container 602 to a hospital bed rail 700. According to an embodiment, a user inserts the end of first appendage portion 502 into an opening 604 of container 602 and pulls protrusion 510 therethrough. The user then inserts the end of first appendage portion 502 into the aperture of first receiving portion 514 and pulls protrusion 510a therethrough to define a loop with first attachment area 512. The user repeats this process with hospital bed rail attachment apparatuses 500a and 500b. The pair of hospital bed rail attachment apparatuses 500a and 500b are thereby securely connected to container 602 (as shown in FIG. 7). To securely attach hospital bed rail attachment apparatuses 500a and 500b, the user wraps a second appendage portion 506 around a circumference of hospital bed rail 700. The user then inserts the end of second appendage portion 506 into the aperture of second receiving portion 516 and pulls protrusion 510b therethrough to define a loop with second attachment area 518. The user repeats this process with hospital bed rail attachment apparatuses 500a and 500b. The pair of hospital bed rail attachment apparatuses 500a and 500b are thereby securely connected to hospital bed rail 700 (as shown in FIG. 7). To disconnect hospital bed rail attachment apparatuses 500a and 500b from container 602, the user pulls protrusion 510a back through the aperture of first receiving portion 514 to disconnect the loop defined by first attachment area 512. To disconnect hospital bed rail attachment apparatuses 500a and 500b from hospital bed rail 700, the user pulls protrusion 510b back through the aperture of second receiving portion 516 to disconnect the loop defined by second attachment area 518. Hospital bed rail attachment apparatuses 500a and 500b may be wiped clean for future use or discarded and replaced when contaminated.

Figure 8:
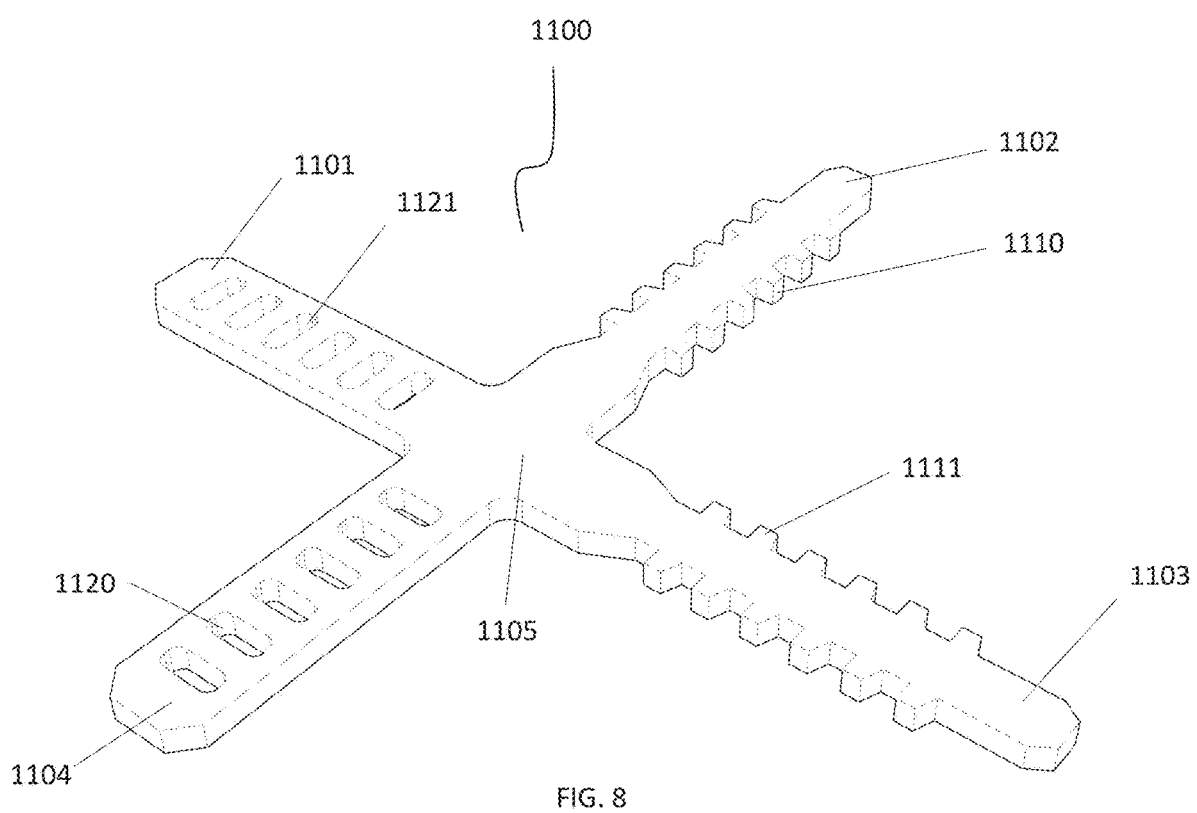
FIG. 8 is a perspective view of the multi-orientation strap apparatus according to an embodiment of the present disclosure.

Referring now to FIG. 8, a top perspective view of the multi-orientation strap apparatus 1100 is shown. According to an embodiment, multi-orientation strap apparatus 1100 is generally comprised of a first appendage 1103, a second appendage 1101, a third appendage 1102, a fourth appendage 1104, a center portion 1105, protrusions 1111 disposed on the first appendage, receiving portions 1121 disposed on the second appendage, protrusions 1110 disposed on the third appendage, and receiving portions 1120 being integrally incorporated into the fourth appendage. The multi-orientation strap apparatus 1100 may be constructed of rubber, silicone or another form of elastomeric material. The elastomeric material of the multi-orientation strap apparatus 1100 may be alternatively constructed, at least partially, from a flexible antimicrobial substance and/or be surface coated with an antimicrobial coating/formulation. Appendage connection portions 1101, 1102, 1103, and 1104 may be seamlessly connected to the central portion 1105 and may extend radially therefrom. In accordance with certain embodiments, first appendage 1103 may be comprised of twelve spaced protrusions 1111 located at the edge of appendage 1103 and molded into appendage 1103 in a linear consecutive arrangement. First appendage 1103 may be alternatively constructed to comprise greater or fewer protrusions, depending on the length of first appendage 1103. Protrusions 1111 may be rectangular in shape, although other shapes are readily anticipated. For example, protrusions 1111 may be alternatively constructed in various shapes, such as cylindrical, irregular, star-shaped, and the like.

Figure 10:
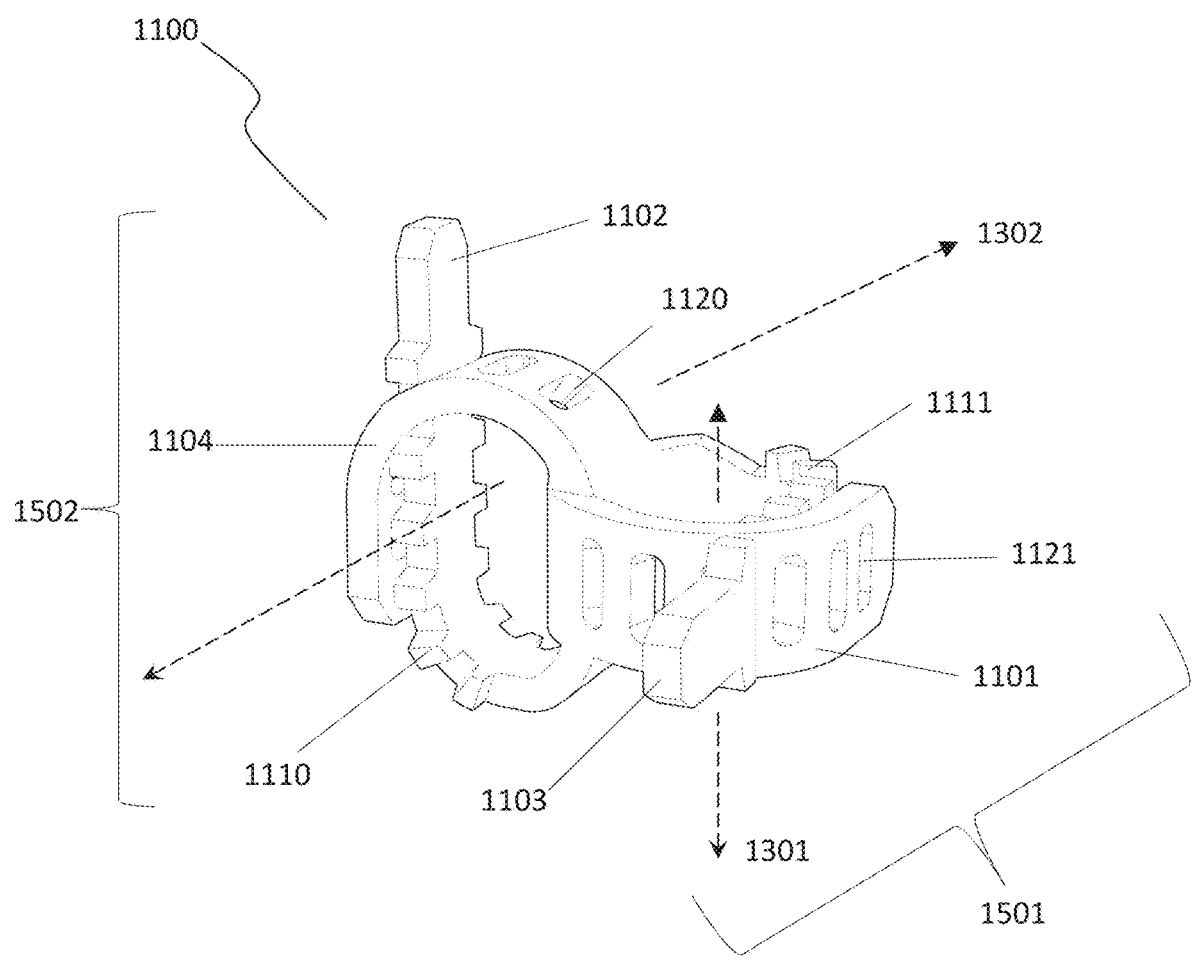
FIG. 10 is a perspective view of the multi-orientation strap apparatus configured for use, according to an embodiment.

In accordance with certain embodiments, second appendage 1101 may comprise six spaced receiving portions 1121 molded into the appendage in a linear consecutive arrangement. Second appendage 1101 may be alternatively constructed to contain greater or fewer openings depending on the length of second appendage 1101. In accordance with certain exemplary use cases, first appendage 1103 may be pulled through a chosen receiving portion 1121 to define a loop 1501 (as shown in FIG. 10). Protrusions 1111 of first appendage 1103 may be greater in width than that of receiving portions 1121 to enable protrusions 1111 to be friction-secured to receiving portions 1121 when pulled therethrough. Multi-orientation strap apparatus 1100 should be constructed of an elastomeric material having a Shore durometer and surface roughness/tack sufficient to enable protrusions 1111 to temporarily deform and/or be displaced to enable protrusions 1111 to be pulled through the aperture of the chosen receiving portion 1121. Protrusions 1111 may be configured to have a width/size sufficient to enable protrusions 1111 to be securely coupled to receiving portion 1121 by preventing protrusions 1111 from readily passing back through the aperture of the receiving portion 1121, thereby enabling a buckling action to secure the multi-orientation strap apparatus 1100 to a target object, surface, and/or circumference, such as an IV Pole, IV tubing, or other apparatus.

In accordance with certain embodiments, third appendage 1102 may comprise twelve spaced protrusions 1110 located at an edge of appendage 1102 molded into third appendage 1102 in a linear consecutive arrangement. Third appendage 1102 may be alternatively constructed to contain greater or fewer protrusions, depending on the length of third appendage 1102. Protrusions 1110 may be rectangular in shape, although alternative shapes are readily anticipated. For example, protrusions 1110 may be alternatively constructed in various shapes, such as cylindrical, irregular, star-shaped, and the like.

Fourth appendage 1104 may comprise six spaced receiving portions 1120 molded into the appendage in a linear consecutive arrangement. Fourth appendage 1104 may be alternatively constructed to contain greater or fewer openings depending on the length of fourth appendage 1104. In accordance with certain exemplary use cases, third appendage 1102 may be pulled through the chosen receiving portions 1120 to create the desired sized loop 1502 (as shown in FIG. 10). Protrusions 1110 of third appendage 1102 may be greater in width than that of receiving portions 1120 to enable protrusions 1110 to be friction-secured to receiving portions 1120 when pulled therethrough. The elastomeric material allows the protrusions 1110 to be pulled through the aperture of the receiving portion 1120. The greater width of the protrusions 1110 enables protrusions 1110 to be securely coupled to receiving portion 1120 by preventing protrusions 1110 from readily passing back through the aperture of the receiving portion 1120, thereby enabling a buckling action to secure the multi-orientation strap apparatus 1100 to a target object, surface, and/or circumference, such as an IV Pole, IV tubing, or other apparatus.

Figure 9:
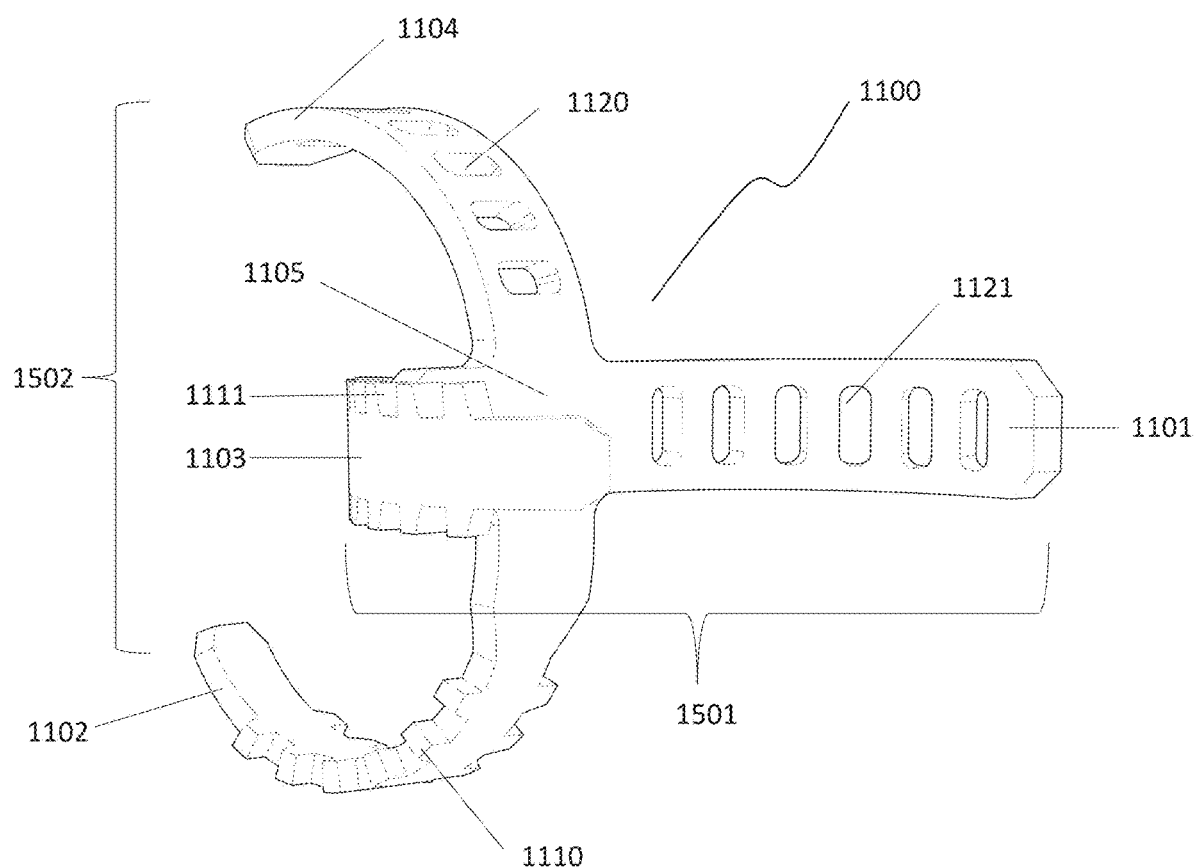
FIG. 9 is a perspective view of the multi-orientation strap apparatus according to an embodiment of the present disclosure.

Referring now to FIG. 9, a perspective view of the multi-orientation strap apparatus 1100 demonstrates the flexibility of the first and second appendage pair 1501 and the third and fourth appendage pair 1502 in multiple orientations around the center portion 1105. According to an embodiment of the present disclosure, appendages 1501 and/or 1502 may be configured to define one or two loops in accordance with a first and second orientation. Appendage pair 1501 may be positioned 90 degrees from appendage pair 1502.

Referring now to FIG. 10, a perspective view of the multi-orientation strap apparatus 1100 forming two loops is shown. In accordance with certain embodiments, loop 1501 may be configured by (i) aligning the appendage 1101 to appendage 1103; (ii) inserting the free end of appendage 1103 into the chosen receiving portion 1121; and (iii) pulling appendage 1103 through the chosen receiving portion 1121 until the chosen protrusion 1111 has engaged the receiving portion 1121 to create a buckled position. In accordance with certain embodiments, loop 1502 may be configured by (i) aligning the appendage 1104 to appendage 1102; (ii) inserting the free end of appendage 1102 into the chosen receiving portion 1120; and (iii) pulling appendage 1102 through the chosen receiving portion 1120 until the chosen protrusion 1110 has engaged the receiving portion 1120 to create a tight buckled position. Multi-orientation strap apparatus 1100 may be engaged in a double loop configuration by orienting loop 1501 and loop 1502 concomitantly. When configured in a double loop configuration, multi-orientation strap apparatus 1100 enables secure attachment to two separate circumferences; for example, a vertical circumference 1301 through loop 1501 and a horizontal circumference 1302 through loop 1502.

Figure 11:
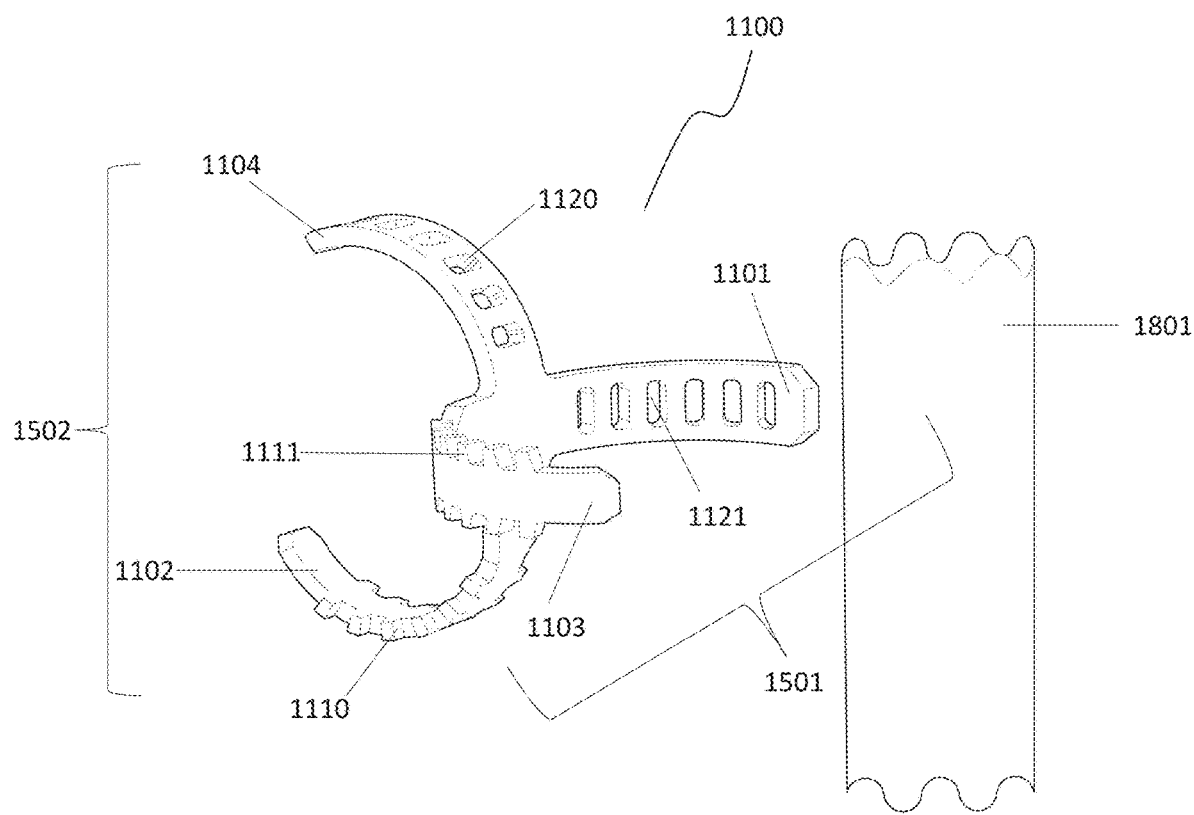
FIG. 11 is a perspective view of the multi-orientation strap apparatus orientated for a vertical circumference, according to an embodiment.
Figure 12:
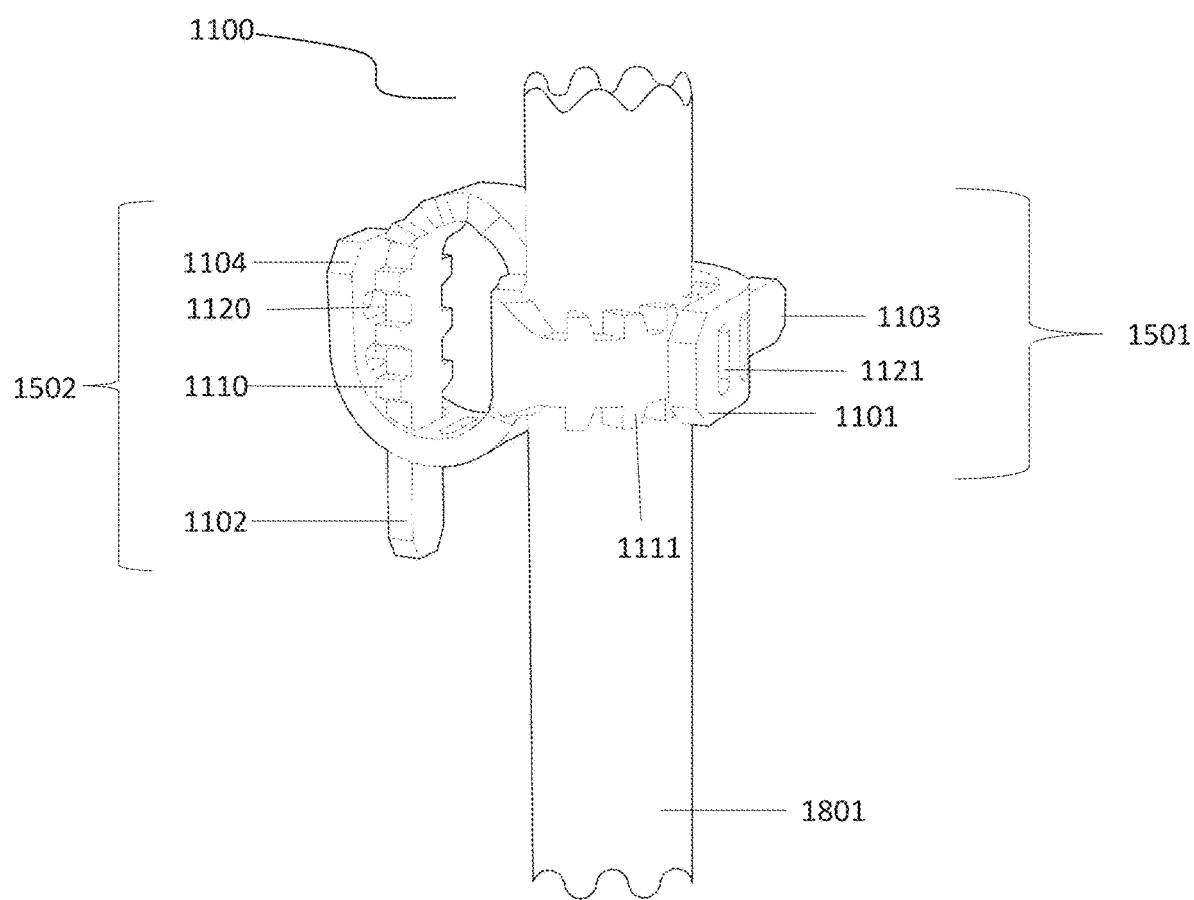
FIG. 12 is a perspective view of the multi-orientation strap apparatus configured for use around a vertical circumference, according to an embodiment.

Referring now to FIG. 11, a perspective view of multi-orientation strap apparatus 1100 selectively coupled to a vertical circumference 1801 is shown. In accordance with an embodiment, multi-orientation strap apparatus 1100 may be selectively affixed to a vertical circumference 1801 by (i) aligning appendage 1101 and appendage 1103 to be perpendicularly wrapped around the vertical surface; (ii) inserting the free end of appendage 1103 into the chosen receiving portion 1121; and (iii) pulling appendage 1103 through the chosen receiving portion 1121 until the chosen protrusion 1111 has engaged the receiving portion 1121 to create a tight buckled position. Multi-orientation strap apparatus 1100 may be selectively secured to the vertical circumference 1801, as shown in FIG. 12. The surface of the vertical circumference 1801 may be alternatively constructed in various shapes, such as cylindrical, irregular, rectangular, and the like.

Figure 13:
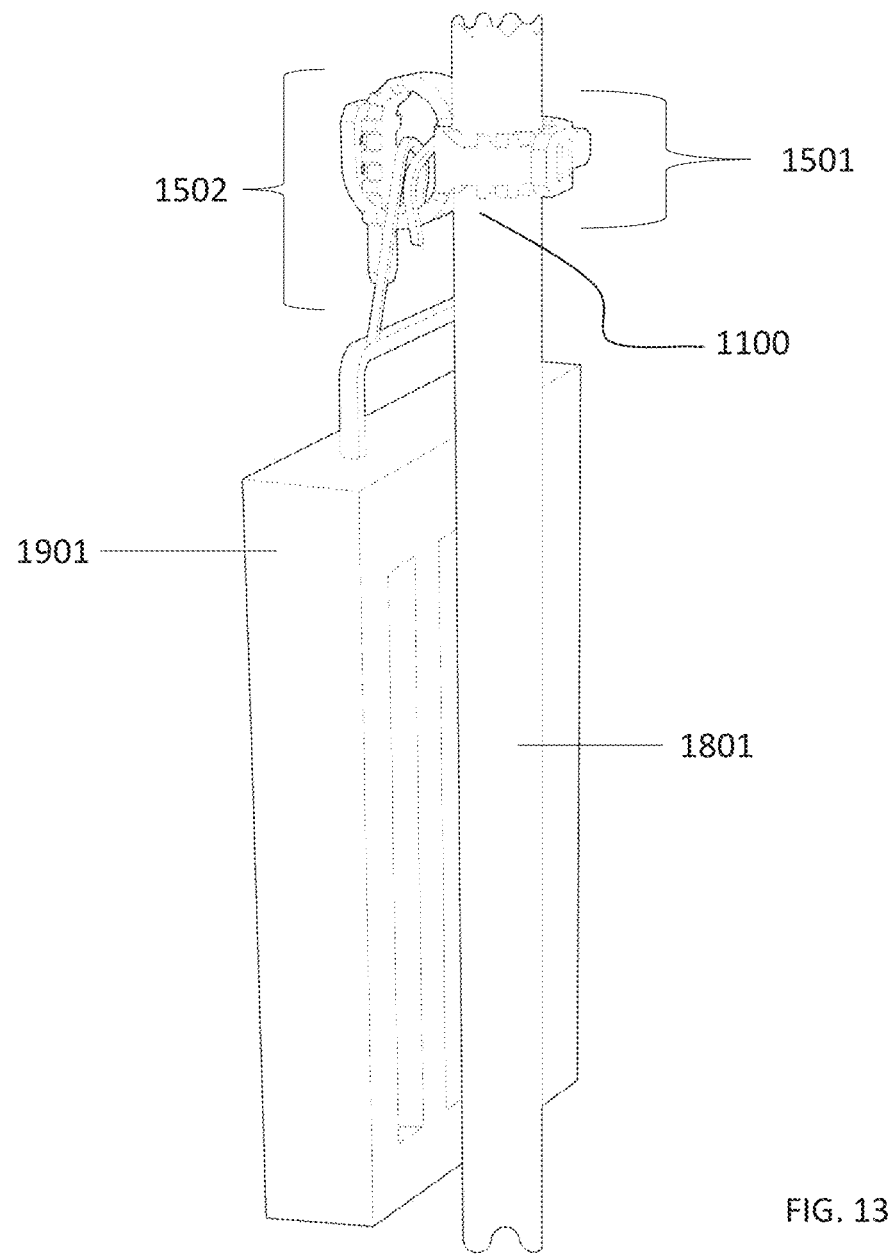
FIG. 13 is a perspective in-use view of the multi-orientation strap apparatus configured around a vertical circumference and fully utilized, according to an embodiment.

Referring now to FIG. 13, a perspective view of multi-orientation strap apparatus 1100 securely attached to a vertical circumference is shown. In accordance with an embodiment, loop 1501 is securely attached to vertical circumference 1801 while loop 1502 is formed to receive horizontal circumferences, such as IV tubing, or one or more hooks, such as a chest drainage box 1901. Multi-orientation strap apparatus 1100 may be manufactured to ensure the weight of medical devices can be adequately supported.

Figure 14:
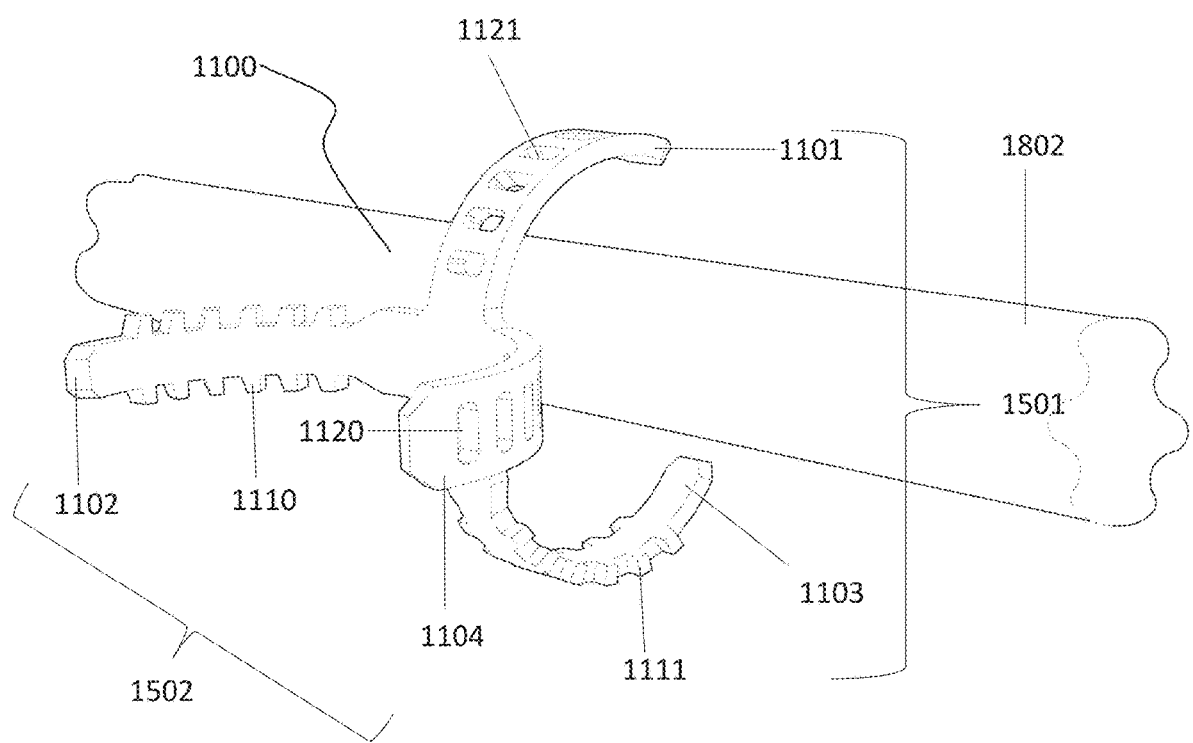
FIG. 14 is a perspective view of the multi-orientation strap apparatus orientated for a horizontal circumference, according to an embodiment.

Referring now to FIG. 14, a perspective view of multi-orientation strap apparatus 1100 being operably engaged with a horizontal circumference 1802 is shown. In accordance with an embodiment, loop 1502 (as shown in FIG. 10) may be selectively coupled to a horizontal surface, or multi-orientation strap apparatus 1100 can be rotated by 90 degrees along the X-axis to allow loop 1501 to be attached to a horizontal circumference 1802, as shown in FIG. 14. As shown in FIG. 14, multi-orientation strap apparatus 1100 may be selectively affixed to horizontal circumference 1802 by (i) aligning appendage 1101 and appendage 1103 to perpendicularly wrap around the horizontal surface; (ii) inserting the free end of appendage 1103 into the chosen receiving portion 1121; and (iii) pulling appendage 1103 through the chosen receiving portion 1121 until the chosen protrusion 1111 has engaged the receiving portion 1121 to create a tight buckled position. Multi-orientation strap apparatus 1100 may be selectively secured to the horizontal circumference 1802, as shown in FIG. 15.

Figure 15:
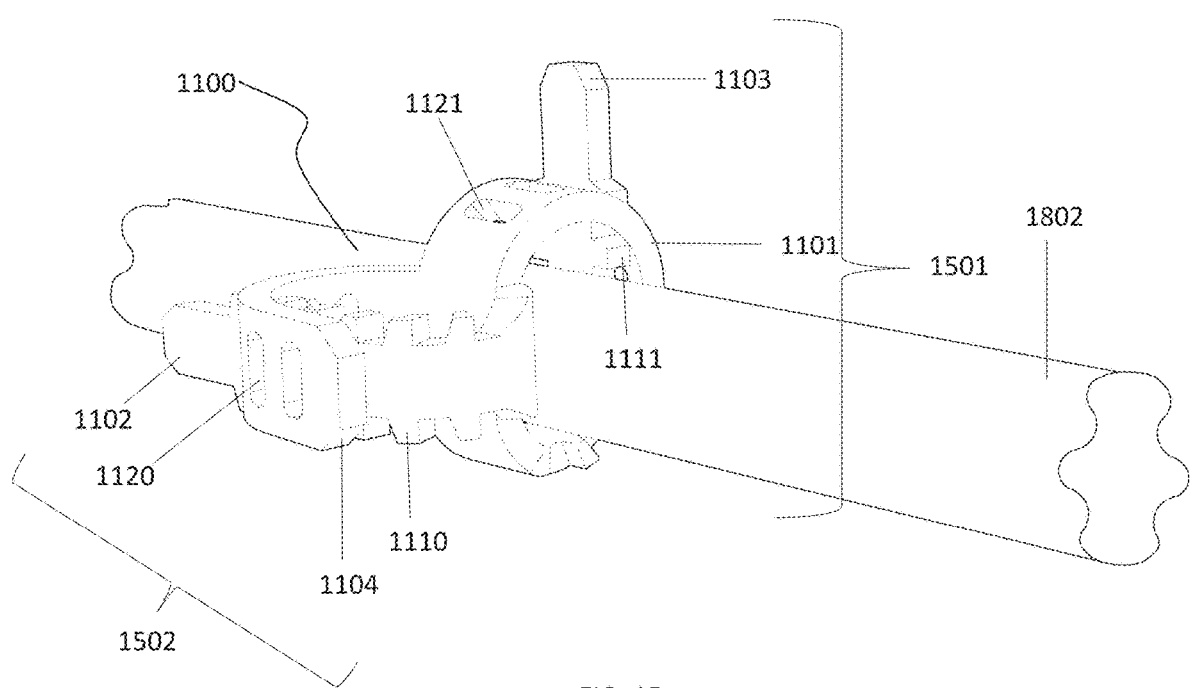
FIG. 15 is a perspective view of the multi-orientation strap apparatus configured for use around a horizontal circumference, according to an embodiment.
Figure 16:
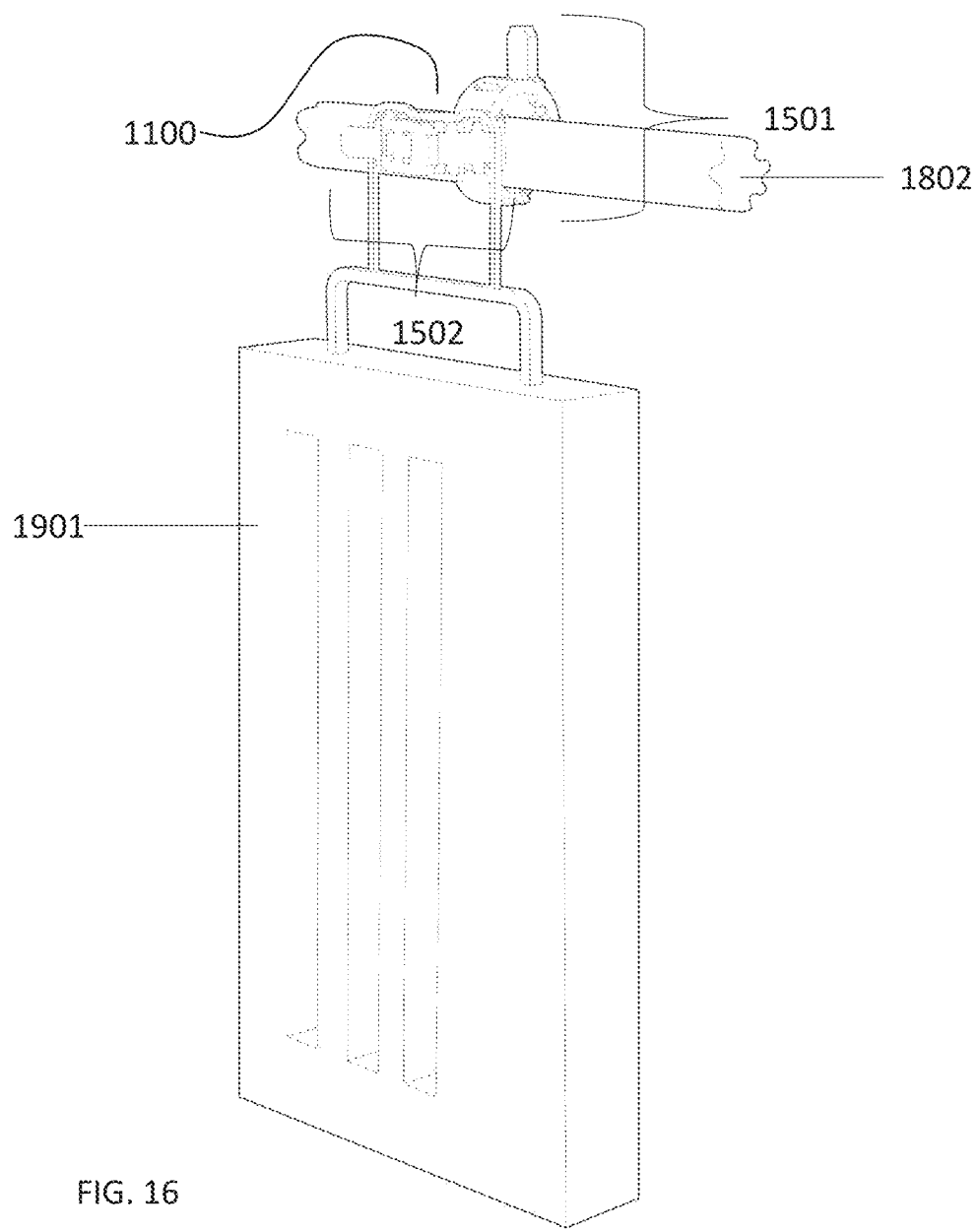
FIG. 16 is a perspective in-use view of the multi-orientation strap apparatus configured around a horizontal circumference and fully utilized, according to an embodiment.

Referring now to FIG. 15, a perspective view of multi-orientation strap apparatus 1100 selectively coupled to horizontal circumference 1802 is shown. In accordance with an embodiment, loop 1501 may be selectively coupled to horizontal circumference 1802 while loop 1502 may be selectively configured to receive vertical circumferences, such as IV tubing, or one or more hooks, such as a chest drainage box 1901, as shown in FIG. 16. Multi-orientation strap apparatus 1100 may be selectively disengaged/removed from either vertical circumference 1801 or horizontal surface 1802 by pulling protrusion 1111 back through the aperture of first receiving portion 1121 to disconnect the loop defined by first attachment area 1501. To disconnect loop 1502, the user pulls protrusion 1110 back through the aperture of receiving portion 1120 to disconnect the loop defined by second attachment area 1502. Upon disengagement/removal from a target surface, multi-orientation strap apparatus 1100 may be wiped clean/disinfected for future use or discarded and replaced if contaminated.

Multi-orientation strap apparatus 1100 may be manufactured of an elastomeric polymer having a Shore durometer configured to enable a desired tensile and elastic strength to securely suspend a desired object being selectively coupled to multi-orientation strap apparatus 1100 in accordance with various intended use cases. In accordance with certain embodiments, multi-orientation strap apparatus 1100 may be constructed of an elastomeric polymer having a Shore durometer in the range of about 15 to about 50. In accordance with a first exemplary use case where multi-orientation strap apparatus 1100 may be utilized to secure IV tubes to an IV pole, multi-orientation strap apparatus 1100 may be constructed of an elastomeric polymer having a Shore durometer of about 20. In accordance with a second exemplary use case where multi-orientation strap apparatus 1100 may be utilized to secure a chest drainage box (as shown in FIG. 16), multi-orientation strap apparatus 1100 may be constructed of an elastomeric polymer having a Shore durometer in the range of about 30 to about 50. Multi-orientation strap apparatus 1100 may be manufactured of an elastomeric polymer having a surface roughness or surface tack being configured to enable a range of support strengths when coupled to a target surface, in accordance with various exemplary use cases.

Figure 17:
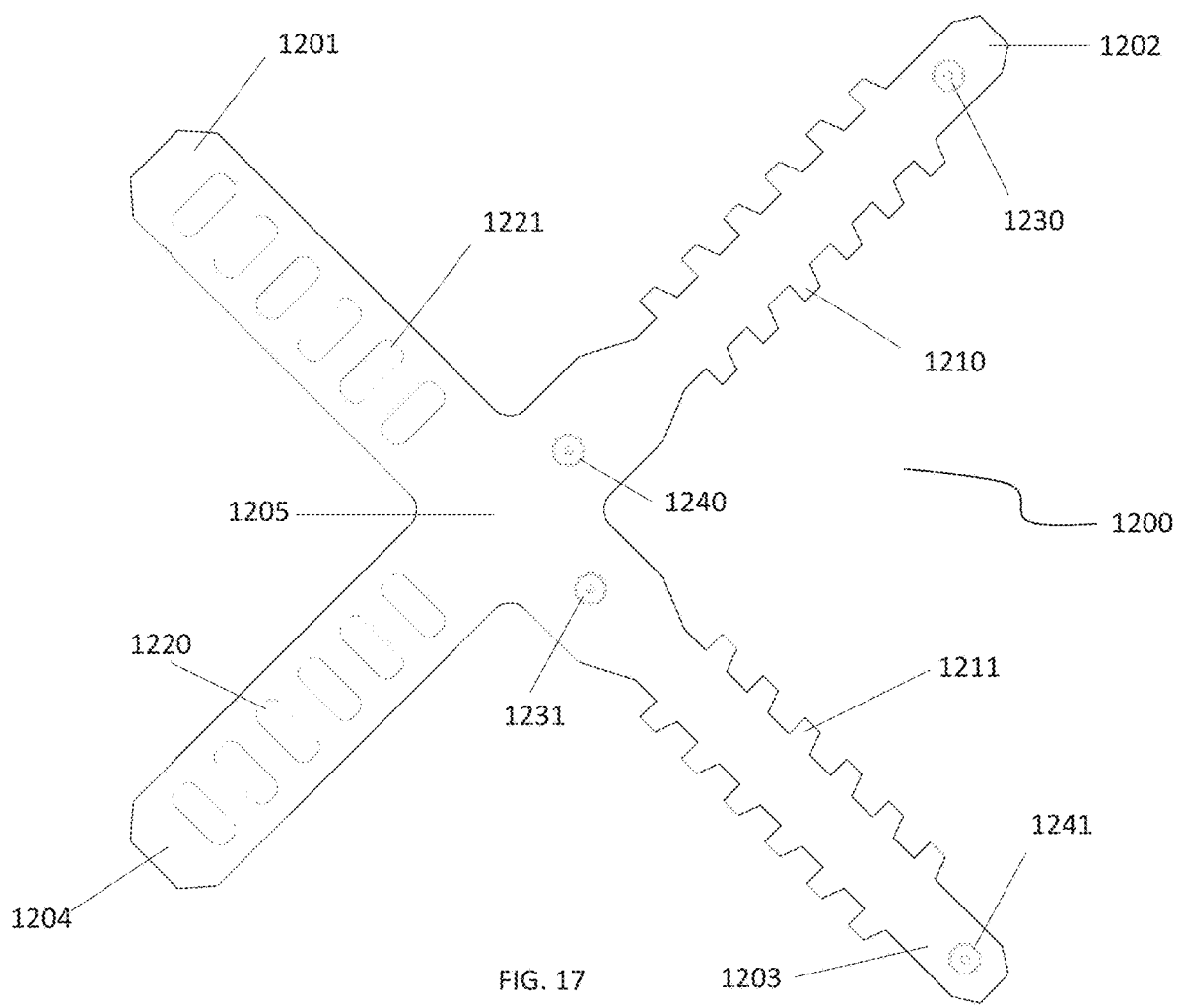
FIG. 17 is a top view of the multi-orientation strap apparatus, according to an embodiment.

Referring now to FIG. 17, a top view of another embodiment of the multi-orientation strap apparatus 1200 is shown. According to an embodiment, device 1200 is generally comprised of a first appendage 1203, a second appendage 1201, a third appendage 1202, a fourth appendage 1204, a center portion 1205, protrusions 1211 located on the first appendage, receiving portions 1221 located on the second appendage, protrusions 1210 located on the third appendage, and receiving portions 1220 located on the fourth appendage. Multi-orientation strap apparatus 1200 may be constructed of silicone or another form of rubber or elastomeric polymer or material. The elastomeric material of the multi-orientation strap apparatus 1200 may be constructed, at least partially, from a flexible antimicrobial substance and/or may comprise a surface coating of an antimicrobial formulation. Appendage connection portions 1201, 1202, 1203, and 1204 may be seamlessly connected to the central portion 1205 and extend radially therefrom. In accordance with certain embodiments, first appendage 1203 may comprise twelve spaced protrusions 1211 located at an edge of appendage 1203 and molded into appendage 1203 in a linear consecutive arrangement. First appendage 1203 may be alternatively constructed to comprise greater or fewer protrusions, depending on the length of first appendage 1203. Protrusions 1211 may be rectangular in shape; however, it is readily anticipated that protrusions 1211 may be alternatively constructed in various shapes, such as cylindrical, irregular, star-shaped, and the like. Second appendage 1201 may comprise six receiving portions 1221 being approximately equidistantly shaped and molded into second appendage 1201 in a linear consecutive arrangement. Second appendage 1201 may be alternatively constructed to comprise greater or fewer openings depending on the length of second appendage 1201. In accordance with certain embodiments, multi-orientation strap apparatus 1200 may comprise two fasteners, each with a negative portion and a positive portion, being configured such that when the negative portion interlocks with the positive portion a secure bond occurs. First negative portion 1230 may be located at the end of appendage portion 1202 with its partner positive portion 1240 located at the central end of appendage 1202. Second negative portion 1231 may be located at the central end of appendage 1203 with its partner positive portion 1241 located at the end of appendage 1203.

Figure 18:
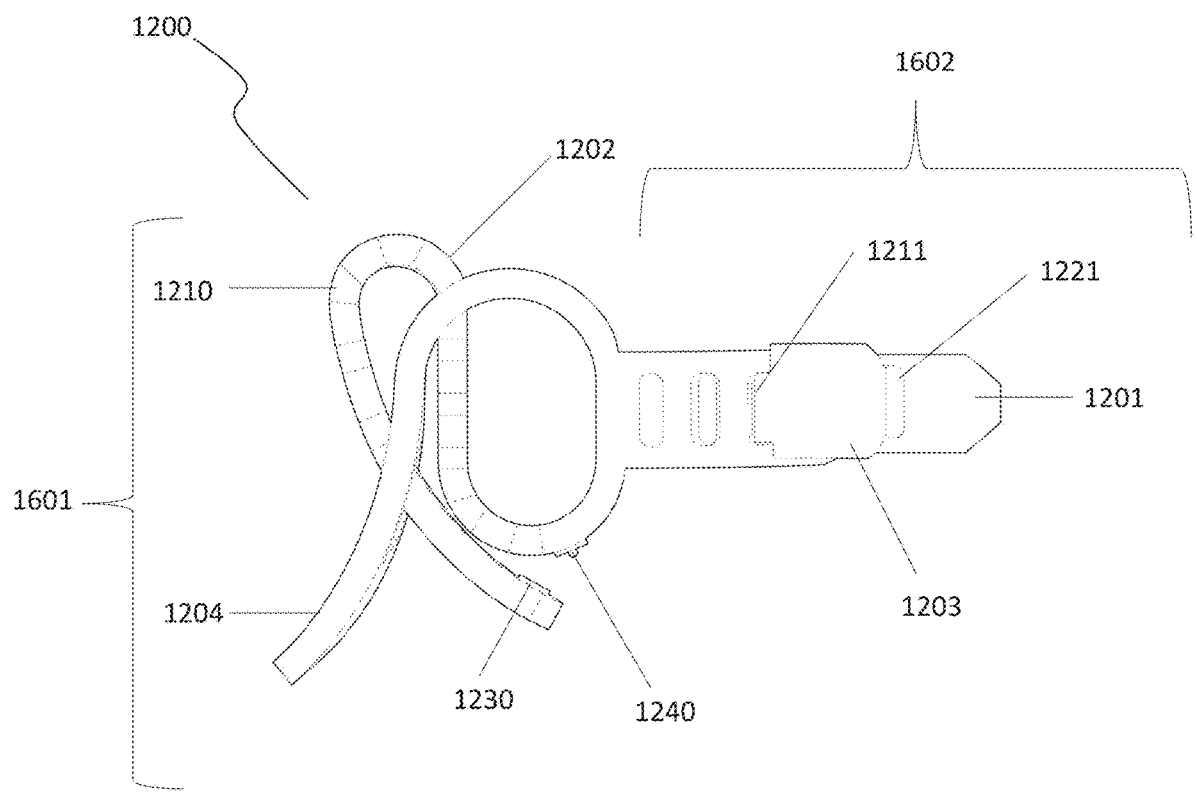
FIG. 18 is a side view of the multi-orientation strap apparatus configured and secured, according to an embodiment.
Figure 19:
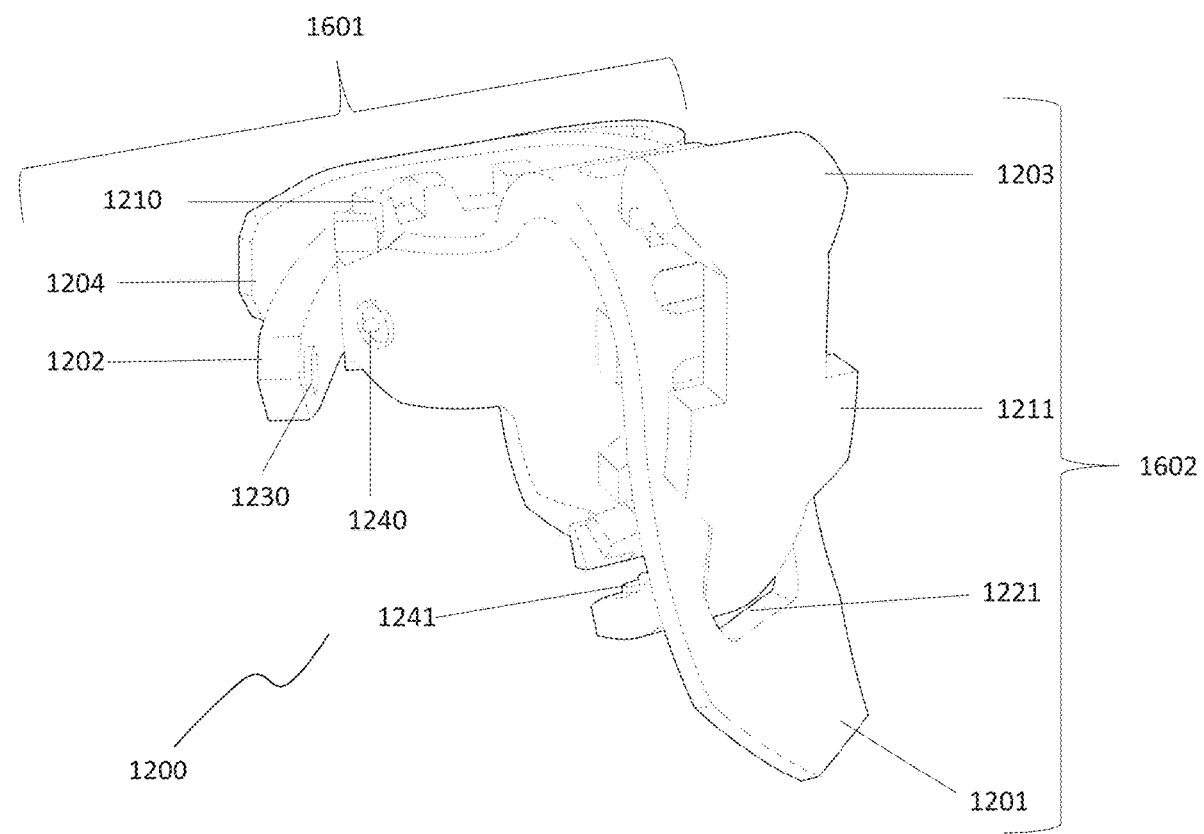
FIG. 19 is a perspective view of the multi-orientation strap apparatus configured and secured, according to an embodiment.

Referring now to FIG. 18, a side view of multi-orientation strap apparatus 1200 is shown. According to an embodiment, multi-orientation strap apparatus 1200 may be configured by the user in such that loop 1601 and loop 1602 may be selectively locked in respective loop configurations. Loop 1601 may be selectively defined by aligning appendage portion 1202 to appendage portion 1204 and weaving the end of appendage 1202 through two or more receiving portions 1220 (not shown), located on appendage portion 1204, such that the end of appendage portion 1202 doubles back on itself to define a double-buckle configuration. In accordance with said embodiment, negative fastener portion 1230 is aligned with positive fastener portion 1240 until securely bonded. Second loop portion 1602 may be defined by aligning appendage portion 1203 to appendage portion 1201 and weaving the end of appendage 1203 through two or more receiving portions 1221, located on appendage portion 1201, such that the end of appendage portion 1203 may double back on itself to define a double-buckle configuration. In accordance with said embodiment, negative fastener portion 1231 (not shown) is aligned with positive fastener portion 1241 until securely bonded (as shown in FIG. 19).

The present disclosure includes that contained in the appended claims as well as that of the foregoing description. Although this invention has been described in its exemplary forms with a certain degree of particularity, it is understood that the present disclosure has been made only by way of example and numerous changes in the details of construction and combination and arrangement of parts may be employed without departing from the spirit and scope of the invention.

What is claimed is:

1. A multi-orientation strap apparatus comprising:
 a unitary body constructed of an elastomeric material comprising a surface coating of an antimicrobial formulation, the unitary body comprising:
  a first appendage portion,
  a second appendage portion,
  a third appendage portion,
  a fourth appendage portion, and
  a central portion located between the first appendage portion and the second appendage portion and between the third appendage portion and the fourth appendage portion;
 a plurality of protrusions linearly disposed in a consecutive arrangement along opposing edges of each of the first appendage portion and the third appendage portion, the plurality of protrusions being substantially rectangular in shape;
  wherein the second appendage portion extends from the central portion and is oppositely oriented from the first appendage portion, the second appendage comprising a first attachment portion configured to receive at least one protrusion in the plurality of protrusions disposed on the first appendage portion;

wherein the first appendage portion is selectively configured to extend through the first attachment portion of the second appendage portion to define a loop;

wherein the fourth appendage portion extends from the central portion and is oppositely oriented from the third appendage portion, the fourth appendage portion comprising a second attachment portion configured to receive at least one protrusion in the plurality of protrusions disposed on the third appendage portion; and wherein the third appendage portion is selectively configured to extend through the second attachment portion of the fourth appendage portion to define a loop;

a first fastener disposed on the first appendage portion, the first fastener comprising a first negative portion and a first positive portion configured to securely interface with each other, wherein the first negative portion and the first positive portion are oppositely oriented on the first appendage portion; and a second fastener disposed on the third appendage portion, the second fastener comprising a second negative portion and a second positive portion configured to securely interface with each other, wherein the second negative portion and the second positive portion are oppositely oriented on the third appendage portion.

2. The multi-orientation strap apparatus of claim 1 wherein at least the first appendage portion with the second appendage portion is configured to be selectively coupled around a target surface.

3. The multi-orientation strap apparatus of claim 2 wherein at least the third appendage portion with the fourth appendage portion is configured to be selectively coupled around a target surface.

4. The multi-orientation strap apparatus of claim 1 wherein at least the third appendage portion with the fourth appendage portion is configured to be selectively coupled around a target surface.

5. The multi-orientation strap apparatus of claim 1 wherein at least one protrusion in the plurality of protrusions disposed on the first appendage portion is mateably engaged with the first attachment portion of the second appendage portion.

6. The multi-orientation strap apparatus of claim 1 wherein at least one protrusion in the plurality of protrusions disposed on the third appendage portion is mateably engaged with the second attachment portion of the fourth appendage portion.

7. The multi-orientation strap apparatus of claim 1 further comprising at least one fastener disposed on the unitary body.

8. The multi-orientation strap apparatus of claim 7 further comprising at least one fastener disposed on at least one appendage portion.

9. The multi-orientation strap apparatus of claim 1 wherein the elastomeric material of the multi-orientation strap apparatus comprises silicone.

10. The multi-orientation strap apparatus of claim 1 wherein the appendage portions extend outwardly from the central portion such that the unitary body defines an X-shape.

11. The multi-orientation strap apparatus of claim 10 wherein the plurality of protrusions comprises twelve protrusions molded along opposite edges of the first appendage portion.

12. A multi-orientation strap apparatus comprising:
a unitary body;
a central portion, and
a first appendage, a second appendage, a third appendage, and a fourth appendage, the appendages extending outwardly from the central portion such that the unitary body defines an X-shape;

a plurality of protrusions disposed on each of the first appendage and the second appendage, the plurality of protrusions being linearly disposed between an outer end portion and a central end portion of each of the first appendage and the second appendage;

a plurality of apertures disposed on each of the third appendage and the fourth appendage,
wherein each protrusion in the plurality of protrusions is configured to selectively interface with each aperture in the plurality of apertures; and a first fastener disposed on the first appendage, the first fastener comprising a first negative portion and a first positive portion configured to securely interface with each other, wherein the first negative portion and the first positive portion are oppositely located on the outer end portion and the central end portion of the first appendage; and a second fastener disposed on the second appendage, the second fastener comprising a second negative portion and a second positive portion configured to securely interface with each other, wherein the second negative portion and the second positive portion are oppositely located on the outer end portion and the central end portion of the second appendage.

13. The multi-orientation strap apparatus of claim 12 wherein the first appendage is selectively coupled to the third appendage to define a loop.

14. The multi-orientation strap apparatus of claim 12 wherein the second appendage is selectively coupled to the fourth appendage to define a loop.

15. The multi-orientation strap apparatus of claim 12 wherein the multi-orientation strap apparatus is constructed of an elastomeric material having a Shore durometer in a range of from 15 to 50 and comprising a surface coating of an antimicrobial formulation.

16. The multi-orientation strap apparatus of claim 12 wherein:
the plurality of protrusions are rectangular in shape and linearly disposed between the outer end portion and the central end portion of each of the first appendage and the second appendage in a consecutive arrangement so as to protrude from opposing sides of each of the first appendage and the second appendage; and the plurality of apertures linearly disposed on each of the third appendage and the fourth appendage are oblong in shape with a direction of elongation of each of the plurality of apertures being transverse to a direction of elongation of the third appendage and the fourth appendage.

17. A multi-orientation strap apparatus comprising:
at least four appendages coupled together to define a unitary body,
wherein a first pair of appendages in the at least four appendages are selectively coupled together to define a first loop, and a second pair of appendages in the at least four appendages are selectively coupled together to define a second loop, the first loop and the second loop being oppositely oriented,
wherein the first pair of appendages are selectively coupled together by a plurality of protrusions disposed in a linear consecutive arrangement on a first appendage of the first pair of appendages and a plurality of apertures disposed in a linear consecutive arrangement on a second appendage of the first pair of appendages, wherein the second pair of appendages in the at least four appendages are selectively coupled together by a plurality of protrusions disposed in a linear consecutive arrangement on a first appendage of the second pair of appendages and a plurality of apertures disposed a linear consecutive arrangement on a second appendage of the second pair of appendages, wherein the plurality of apertures are oblong in shape in a direction transverse to a direction of elongation of the appendages; and a first fastener disposed on the first appendage of the first pair of appendages, the first fastener comprising a first negative portion and a first positive portion configured to securely interface with each other, wherein the first negative portion and the first positive portion are oppositely oriented on the first appendage of the first pair of appendages; and a second fastener disposed on the first appendage of the second pair of appendages, the second fastener comprising a second negative portion and a second positive portion configured to securely interface with each other, wherein the second negative portion and the second positive portion are oppositely oriented on the first appendage of the second pair of appendages.

18. The multi-orientation strap apparatus of claim 17 wherein the at least four appendages are configured as an X-shape.

19. The multi-orientation strap apparatus of claim 17 wherein the multi-orientation strap apparatus is constructed of an elastomeric material comprising a surface coating of an antimicrobial formulation.

20. The multi-orientation strap apparatus of claim 17 wherein the plurality of protrusions are rectangular in shape and protrude from opposing sides of the appendages.

* * * * *